United States Patent
Lim et al.

(10) Patent No.: US 12,364,404 B2
(45) Date of Patent: Jul. 22, 2025

(54) APPARATUS AND METHOD FOR ESTIMATING BIO-INFORMATION

(71) Applicant: SAMSUNG ELECTRONICS CO., LTD., Suwon-si (KR)

(72) Inventors: Hye Rim Lim, Suwon-si (KR); Sang Yun Park, Hwaseong-si (KR); Chang Mok Choi, Suwon-si (KR); Jae Min Kang, Seoul (KR); Jin Woo Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 850 days.

(21) Appl. No.: 17/377,098

(22) Filed: Jul. 15, 2021

(65) Prior Publication Data

US 2022/0296112 A1 Sep. 22, 2022

(30) Foreign Application Priority Data

Mar. 19, 2021 (KR) .......................... 10-2021-0035852

(51) Int. Cl.
*A61B 5/021* (2006.01)
*A61B 5/00* (2006.01)
*A61B 5/1172* (2016.01)

(52) U.S. Cl.
CPC ........ *A61B 5/02116* (2013.01); *A61B 5/0059* (2013.01); *A61B 5/1172* (2013.01);
(Continued)

(58) Field of Classification Search
CPC . A61B 5/02116; A61B 5/0059; A61B 5/1172; A61B 5/681; A61B 5/6815;
(Continued)

(56) References Cited

U.S. PATENT DOCUMENTS

| | | | |
|---|---|---|---|
| 7,029,448 B2 | 4/2006 | Kubo | |
| 7,566,307 B2 | 7/2009 | Inukai et al. | |

(Continued)

FOREIGN PATENT DOCUMENTS

| | | |
|---|---|---|
| CN | 102488503 A | 6/2012 |
| CN | 110786837 A | 2/2020 |

(Continued)

OTHER PUBLICATIONS

Communication issued May 1, 2023 by the Korean Intellectual Property Office in Korean Patent Application No. 10-2021-0035852.

(Continued)

*Primary Examiner* — Tse W Chen
*Assistant Examiner* — Joseph A Tombers
(74) *Attorney, Agent, or Firm* — Sughrue Mion, PLLC

(57) ABSTRACT

An apparatus for estimating bio-information is provided. The apparatus for estimating bio-information includes: a pulse wave sensor configured to measure a pulse wave signal from an object; a force sensor configured to measure force exerted between the object and the pulse wave sensor; and a processor configured to obtain an oscillogram by using the pulse wave signal and the force, to determine a first mean arterial pressure (MAP) based on the obtained oscillogram, to extract additional information in an interval preceding a point of the first MAP of the oscillogram, to obtain a second MAP based on the first MAP and the additional information, and to estimate bio-information based on the obtained second MAP.

20 Claims, 19 Drawing Sheets

(52) U.S. Cl.
CPC ............ *A61B 5/681* (2013.01); *A61B 5/6815* (2013.01); *A61B 5/6898* (2013.01); *A61B 2562/0238* (2013.01)

(58) Field of Classification Search
CPC .......... A61B 5/6898; A61B 2562/0238; A61B 5/02225; A61B 5/7278; A61B 5/02416; A61B 2562/043; A61B 5/6826; A61B 5/6824; A61B 5/684; A61B 5/02007; A61B 5/02108; A61B 5/02125; A61B 5/6803; A61B 5/02241; A61B 5/6843; A61B 5/7275
See application file for complete search history.

(56) References Cited

U.S. PATENT DOCUMENTS

| | | |
|---|---|---|
| 10,398,324 B2 | 9/2019 | Mukkamala et al. |
| 10,813,561 B2 | 10/2020 | Kwon et al. |
| 11,141,073 B2 | 10/2021 | Park et al. |
| 11,234,647 B2 | 2/2022 | Kang et al. |
| 11,633,115 B2 | 4/2023 | Kang et al. |
| 2008/0183232 A1 | 7/2008 | Voss et al. |
| 2010/0249616 A1 | 9/2010 | Donehoo et al. |
| 2018/0279888 A1 | 10/2018 | Wang et al. |
| 2018/0338694 A1 | 11/2018 | Settels |
| 2019/0313979 A1 | 10/2019 | Kang et al. |
| 2020/0000349 A1 | 1/2020 | Lin et al. |
| 2020/0008693 A1 | 1/2020 | Mukkamala et al. |
| 2020/0037956 A1* | 2/2020 | Kang ................... A61B 5/0077 |
| 2020/0196881 A1 | 6/2020 | Zemel |
| 2020/0367760 A1 | 11/2020 | Klaassen et al. |
| 2021/0393150 A1 | 12/2021 | Park et al. |
| 2022/0008009 A1 | 1/2022 | Kang et al. |

FOREIGN PATENT DOCUMENTS

| | | |
|---|---|---|
| JP | 2003-284696 A | 10/2003 |
| JP | 2007-82682 A | 4/2007 |
| KR | 10-2012-0108575 A | 10/2012 |
| KR | 10-2018-0076050 A | 7/2018 |
| KR | 10-2019-0030152 A | 3/2019 |
| KR | 10-2020-0097143 A | 8/2020 |

OTHER PUBLICATIONS

Communication dated Feb. 24, 2022, issued by the European Patent Office in European Application No. 21195569.5.
Communication issued on Dec. 31, 2024 by the State Intellectual Property Office of P.R. China in Chinese Patent Application No. 202110782975.4.

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2021-0035852, filed on Mar. 19, 2021, in the Korean Intellectual Property Office, the entire disclosure of which is incorporated by reference herein for all purposes.

BACKGROUND

1. Field

Example embodiments of the present disclosure relate to an apparatus and a method for estimating bio-information, and technology for cuffless blood pressure estimation.

2. Description of Related Art

General techniques for extracting cardiovascular characteristics, such as blood pressure and the like, without using a pressure cuff include a pulse wave analysis (PWA) method and a pulse wave velocity (PWV) method.

The pulse wave analysis (PWA) method is a method of extracting cardiovascular characteristics by analyzing the shape of a photoplethysmography (PPG) signal or a body surface pressure signal obtained from a peripheral part of the body, e.g., a fingertip, a radial artery, or the like. The blood ejected from the left ventricle causes reflection at areas of large branches, such as the renal arteries and the iliac arteries, and the reflection affects the shape of the pulse wave or body pressure wave measured at the peripheral part of the body. Thus, by analyzing this shape, arterial stiffness, arterial age, aortic artery pressure waveform of the like can be inferred.

The pulse wave velocity (PWV) method is a method of extracting cardiovascular characteristics, such as arterial stiffness, blood pressure, or the like, by measuring a pulse wave transmission time. In this method, a delay (or a pulse transit time (PTT)) between an R-peak (corresponding to the left ventricular contraction interval) of an electrocardiogram (ECG) and a peak of a PPG signal of a finger or the radial artery is measured by measuring the ECG and PPG signals of the peripheral part of the body and a velocity at which the blood from the heart reaches the peripheral part of the body is calculated by dividing an approximate length of the arm by the PTT.

SUMMARY

According to an aspect of an example embodiment, there is provided an apparatus for estimating bio-information, the apparatus including: a pulse wave sensor configured to measure a pulse wave signal from an object; a force sensor configured to measure force exerted between the object and the pulse wave sensor; and a processor configured to obtain an oscillogram by using the pulse wave signal and the force, to determine a first mean arterial pressure (MAP) based on the obtained oscillogram, to extract additional information in an interval preceding a point of the first MAP of the oscillogram, to obtain a second MAP based on the first MAP and the additional information, and to estimate bio-information based on the obtained second MAP.

The pulse wave sensor may include at least one light sensor configured to emit light onto the object; and at least one detector configured to detect light scattered or reflected from the object.

The processor may be further configured to determine, as the first MAP, a force value at a maximum amplitude point in the obtained oscillogram.

The processor may be further configured to determine a peak point in the interval preceding the first MAP, and extract, as the additional information, at least one of an amplitude and a force at the determined peak point, an amplitude and a force at a valley point between the peak point and the point of the first MAP, and an amplitude at the point of the first MAP.

Based on a determination that the peak point does not exist in the interval preceding the first MAP, the processor may be further configured to determine, as the peak point, a maximum amplitude point in an interval preceding the valley point, the valley point being a last valley point before the first MAP.

The processor may be further configured to extract at least two additional information, and obtain the second MAP by applying a ratio between values of the at least two additional information to the first MAP.

The at least two additional information may include the amplitude at the point of the first MAP and the amplitude at the peak point to the first MAP, and the processor is further configured to obtain the second MAP by applying a ratio between the amplitude at the point of the first MAP and the amplitude at the peak point to the first MAP.

The at least two additional information may include the amplitude at the point of the first MAP and the amplitude at the valley point to the first MAP, and the processor is further configured to obtain the second MAP by applying a ratio between the amplitude at the point of the first MAP and the amplitude at the valley point to the first MAP.

The processor may be further configured to estimate the bio-information based on the second MAP by using a bio-information estimation model.

The processor may be further configured to extract at least three additional information including the force at the peak point, and obtain the second MAP based on a ratio between values of at least two additional information of the at least three additional information, and further based on a first value obtained by subtracting a value of the force at the peak point from the first MAP.

The processor may be further configured to obtain the second MAP by applying a ratio, between the amplitude at the point of the first MAP and the amplitude at the peak point, to the first value.

The processor may be further configured to obtain the second MAP by applying a ratio, between the amplitude at the point of the first MAP and the amplitude at the valley point, to the first value.

The processor may be further configured to estimate the bio-information based on the first MAP and the second MAP by using a bio-information estimation model.

The apparatus may further include a sensor position obtainer configured to obtain sensor position information of the pulse wave sensor, the sensor position information indicating a position of the pulse wave sensor on the object, which comes into contact with the pulse wave sensor, and the processor may be further configured to control to guide a user on a contact position of the object based on the sensor position information.

The sensor position obtainer may include a fingerprint sensor configured to obtain a fingerprint image of the object that comes into contact with the pulse wave sensor, and the sensor position obtainer is further configured to obtain the sensor position information based on the fingerprint image obtained by the fingerprint sensor.

The sensor position obtainer may be further configured to obtain the sensor position information based on an image of the object that comes into contact with the pulse wave sensor, the image being acquired by an external image capturing device.

The pulse wave sensor may have a plurality of channels for measuring pulse wave signals at a plurality of points of the object, and the processor may be further configured to select at least one channel of the plurality of channels based on a pulse wave signal corresponding to a predetermined position of the object that comes into contact with the pulse wave sensor or based on a pulse wave signal having a noise level less than or equal to a predetermined level, and obtain the oscillogram based on the pulse wave signal obtained by the selected at least one channel.

The bio-information may include at least one of blood pressure, vascular age, arterial stiffness, aortic pressure waveform, vascular compliance, stress index, fatigue level, skin age, and skin elasticity.

According to an aspect of an example embodiment, there is provided a method of estimating bio-information, the method including: measuring, by using a pulse wave sensor, a pulse wave signal from an object; measuring force exerted between the object and the pulse wave sensor; obtaining an oscillogram by using the pulse wave signal and the force; determining a first mean arterial pressure (MAP) based on the obtained oscillogram; extracting additional information in an interval preceding a point of the first MAP of the oscillogram; obtaining a second MAP based on the first MAP and the additional information; and estimating bio-information based on the obtained second MAP.

The determining of the first MAP may include determining a force value at a maximum amplitude point in the obtained oscillogram to be the first MAP.

The extracting the additional information may include determining a peak point in the interval preceding the first MAP, and extracting, as the additional information, at least one of an amplitude and a force at the determined peak point, an amplitude and a force at a valley point between the peak point and the point of the first MAP, and an amplitude at the point of the first MAP.

The extracting the additional information may include, based on a determination that the peak point does not exist in the interval preceding the first MAP, determining, as the peak point, a maximum amplitude point in an interval preceding the valley point, the valley point being a last valley point before the first MAP.

The extracting may include extracting at least two additional information, and the obtaining the second MAP may include obtaining the second MAP by applying a ratio between values of the at least two additional information to the first MAP.

The estimating the bio-information may include estimating the bio-information based on the second MAP by using a bio-information estimation model.

The extracting may include extracting at least three additional information including the force at the peak point, and the obtaining the second MAP may include obtaining the second MAP based on a ratio between values of the at least two additional information of the at least three additional information, and further based on a value obtained by subtracting a value of the force at the peak point from the first MAP.

The estimating the bio-information may include estimating the bio-information based on the first MAP and the second MAP by using a bio-information estimation model.

The method may further include obtaining sensor position information of the pulse wave sensor, the sensor position information indicating a position of the pulse wave sensor on the object, which comes into contact with the pulse wave sensor; and controlling to guide a user on a contact position of the object based on the sensor position information.

According to an aspect of an example embodiment, there is provided an electronic device including an apparatus for estimating bio-information, and an output device configured to output a processing result of the apparatus for estimating bio-information, wherein the apparatus for estimating bio-information includes: a pulse wave sensor configured to measure a pulse wave signal from an object; a force sensor configured to measure force exerted between the object and the pulse wave sensor; and a processor configured to obtain an oscillogram by using the pulse wave signal and the force, to determine a first Mean Arterial Pressure (MAP) based on the obtained oscillogram, to extract additional information in an interval preceding a point of the first MAP of the oscillogram, to obtain a second MAP based on the first MAP and the additional information, and to estimate bio-information based on the obtained second MAP.

The electronic device may include at least one of a wristwatch wearable device, an ear-wearable device, and a mobile device.

The processor may be further configured to determine a peak point in the interval preceding the first MAP, and extract, as the additional information, at least one of an amplitude and a force at the determined peak point, an amplitude and a force at a valley point between the peak point and the point of the first MAP, and an amplitude at the point of the first MAP.

The processor may be further configured to extract at least two additional information, and obtain the second MAP based on a ratio between values of the at least two additional information and the first MAP.

BRIEF DESCRIPTION OF THE DRAWINGS

The above and other aspects, features, and advantages of the disclosure will be more apparent from the following detailed description of example embodiments taken in conjunction with the accompanying drawings, in which.

DETAILED DESCRIPTION

Figure 1:
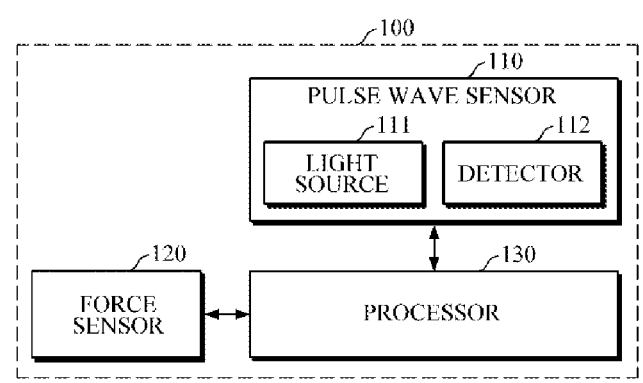
FIG. 1 is a block diagram illustrating an apparatus for estimating bio-information according to an example embodiment.

Details of example embodiments are included in the following detailed description and drawings. Advantages and features of the disclosure, and a method of achieving the same will be more clearly understood from the following example embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Hereinafter, embodiments of an apparatus and a method for estimating bio-information will be described in detail with reference to the accompanying drawings.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

FIG. 1 is a block diagram illustrating an apparatus for estimating bio-information according to an example embodiment.

An apparatus 100 for estimating bio-information, according to various example embodiments which will be described below, may be mounted in terminals, such as a smart phone, a tablet PC, a desktop computer, a laptop computer, etc., wearable devices, and the like. Examples of the wearable devices may include a wristwatch-type wearable device, a bracelet-type wearable device, a wristband-type wearable device, a ring-type wearable device, a glasses-type wearable device, a headband-type wearable device, etc., but the wearable devices are not limited thereto.

Referring to FIG. 1, the apparatus 100 for estimating bio-information according to an embodiment includes a pulse wave sensor 110, a force sensor 120, and a processor 130.

The pulse wave sensor 110 measures a photoplethysmography (PPG) signal (hereinafter referred to as a "pulse wave signal") from an object. The object may be an area of the human body which may come into contact with the pulse wave sensor 110, and may be a body part at which pulse waves may be easily measured by PPG. For example, the object may be a finger where blood vessels are densely distributed, but the object is not limited thereto and may be an area on the wrist that is adjacent to the radial artery, or a peripheral part of the body, such as an upper portion of the wrist, toes, etc., where veins or capillaries are located.

The pulse wave sensor 110 may include one or more light sources 111 configured to emit light onto the object, and one or more detectors 112 which are disposed at a predetermined distance from the light sources 111 and detect light scattered or reflected from the object. The light sources 111 may include a light emitting diode (LED), a laser diode (LD), a phosphor, etc., but are not limited thereto. Further, the detectors 112 may include a photodiode, a photodiode array, a complementary metal-oxide semiconductor (CMOS) image sensor, a charge-coupled device (CCD) image sensor, and the like.

The pulse wave sensor 110 may include the light sources 111 and the detectors 112, which are formed in a single channel, so as to measure a pulse wave signal at a specific point of the object. Alternatively, the pulse wave sensor 110 may include multiple channels to measure a plurality of pulse wave signals at multiple points of the object. The respective channels of the pulse wave sensor 110 may be formed in a pre-defined shape such as a circular shape, an oval shape, a linear shape, etc., so as to measure pulse wave signals at multiple points of the object. Each channel of the pulse wave sensor 110 may include one or more light sources and one or more detectors. Further, each channel may include two or more light sources to emit light of a plurality of wavelengths. Alternatively, the pulse wave sensor 110 may include, for example, one or more light sources and a CMOS image sensor to measure pulse wave signals from a predetermined area of the object.

When a user places an object on the pulse wave sensor 110 and increases or decreases a pressing force to induce a change in a pulse wave amplitude, the force sensor 120 may measure a contact force exerted between the pulse wave sensor 110 and the object. The force sensor 120 may include a strain gauge and the like. The force sensor 120 may be disposed at an upper end or a lower end of the pulse wave sensor 110.

The processor 130 may estimate bio-information based on the pulse wave signal obtained by the pulse wave sensor 110, and the force obtained by the force sensor 120. The bio-information may include, for example, blood pressure, vascular age, arterial stiffness, aortic pressure waveform, vascular compliance, stress index, fatigue level, skin age, skin elasticity, etc., but is not limited thereto. For convenience of explanation, the following description will be made using blood pressure as an example for illustration, but the bio-information is not limited to blood pressure.

Figure 2A:
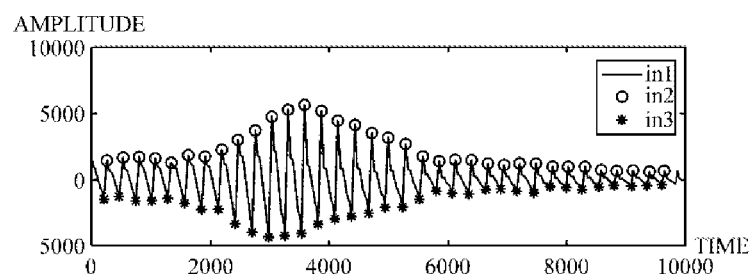
FIGS. 2A and 2B are diagrams explaining an example of estimating blood pressure based on oscillometry.
Figure 2B:
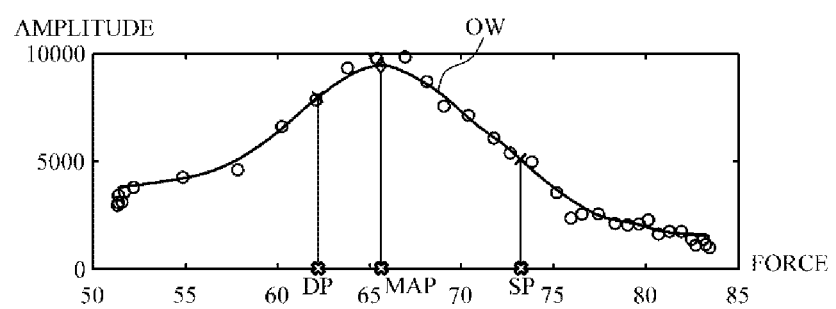
Figure 3A:
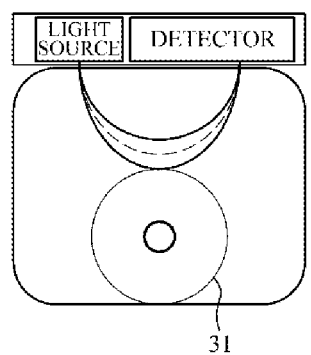
FIG. 3A illustrates a case where a single blood vessel is located in an object and FIG. 3B illustrates a case where a plurality of blood vessels are located in an object.
Figure 4A:
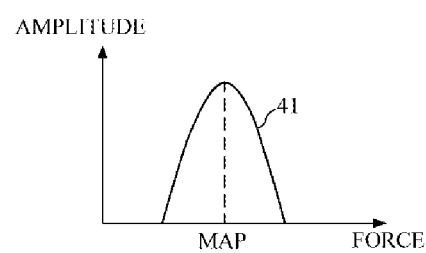
FIGS. 4A and 4B are diagrams illustrating an experimentally obtained oscillogram and an actually observed oscillogram with respect to a single blood vessel according to an example embodiment.
Figure 4B:
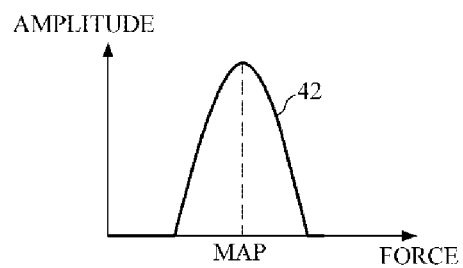
Figure 4C:
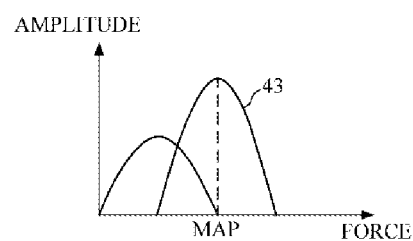
FIGS. 4C and 4D are diagrams illustrating an experimentally obtained oscillogram and an actually observed oscillogram with respect to a plurality of blood vessels according to an example embodiment.
Figure 4D:
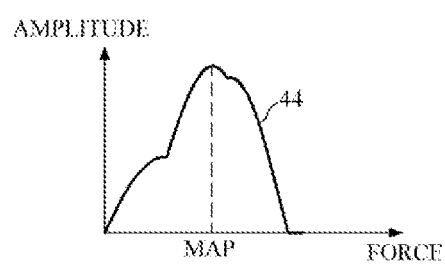

FIGS. 2A and 2B are diagrams explaining an example of estimating blood pressure based on oscillometry. FIGS. 3A and 3B are diagrams illustrating a case where a single blood vessel is located in an object that is in contact with a light source and a detector, and a case where a plurality of blood vessels are located in the object. FIGS. 4A and 4B are diagrams illustrating an experimentally obtained oscillogram and an actually observed oscillogram with respect to a single blood vessel according to an example embodiment. FIGS. 4C and 4D are diagrams illustrating an experimentally obtained oscillogram and an actually observed oscillogram with respect to a plurality of blood vessels according to an example embodiment.

FIGS. 2A and 2B are diagrams explaining an example of estimating blood pressure based on oscillometry.

Referring to FIGS. 2A and 2B, the processor 130 may extract, e.g., a peak-to-peak point of the pulse wave signal waveform by subtracting a negative (−) amplitude value in3 from a positive (+) amplitude value in2 of a waveform envelope in1 at each measurement time point of the pulse wave signal. Further, the processor 130 may obtain an oscillogram (OW) by plotting the peak-to-peak amplitude at each measurement time point against a force value at a corresponding time point and by performing, for example, polynomial curve fitting.

The processor 130 may extract characteristic points for estimating blood pressure from the generated oscillogram OW, and may estimate blood pressure by using the extracted characteristic points. For example, the processor 130 may determine a force value at a maximum amplitude point in the oscillogram OW to be mean arterial pressure (MAP) as a characteristic point, and may extract, as other characteristic points, force values DP, SP, and the like at points corresponding to amplitude values having a preset ratio (e.g., 0.5 to 0.7) to a maximum amplitude value from the oscillogram OW. For example, the processor 130 may determine the MAP itself as a mean blood pressure, and may determine the DP as diastolic blood pressure and the SP as systolic blood pressure. Alternatively, by applying the respective force values MAP, DP, and SP to a pre-defined blood pressure estimation model, the processor 130 may independently estimate the mean blood pressure, the diastolic blood pressure, and the systolic blood pressure. The blood pressure estimation model may be expressed in the form of various linear or non-linear combination functions, such as addition, subtraction, division, multiplication, logarithmic value, regression equation, and the like, with no particular limitation.

Generally, the method of estimating blood pressure based on oscillometry using a finger PPG signal has a drawback in that due to a complicated structure of blood vessels of a finger, blood pressure information of a plurality of blood vessels overlaps, resulting in a single optical signal, such that blood pressure information of a target blood vessel is distorted. For example, an oscillogram measured from an upper arm shows a single peak, but an oscillogram measured from the finger shows a plurality of peaks due to blood vessels with low blood pressure, such that an oscillogram of blood vessels with low blood pressure overlaps an oscillogram of a target blood vessel, such that accuracy in estimating desired blood pressure may be reduced.

Referring to FIG. 4A, with respect to an object including a single blood vessel 31, a point of MAP is obtained in an oscillogram 41, by mathematical modeling based on a change in distance between an optical path and a target blood vessel to be measured, which is caused by skin deformation due to force applied to the target blood vessel. Referring to FIG. 4B, a point MAP is obtained in an oscillogram 42 based on an observed sensitivity of vascular oscillometry according to the change in distance between the optical path and the target blood vessel due to force applied to the target blood vessel, by using an actually measured pulse wave signal as described above with reference to FIGS. 2A and 2B. When FIGS. 4A and 4B are compared with each other, it can be learned that the point of MPA in the oscillogram 41 is in a similar location as the point of MPA in the oscillogram 42 and the respective oscillograms 41 and 42 show a similar shape with a single peak.

Figure 3B:
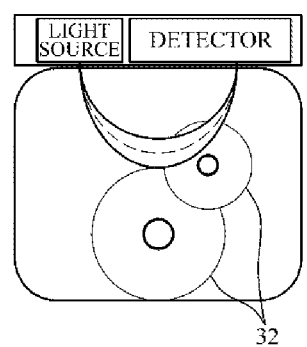

Referring to FIGS. 3B, 4C, and 4D, with respect to an object including a plurality of blood vessels 32, an oscillogram 43 obtained by mathematical modeling of a target blood vessel, and an oscillogram 44 obtained by using an actually measured pulse wave signal show a plurality of peaks. However, due to distortion caused by blood vessels other than the target blood vessel, the point of MAP of the oscillogram 44 may occur at a position relatively ahead of the point of MAP of the oscillogram 43. Accordingly, when blood pressure is estimated for an object, such as a finger, in which a plurality of blood vessels are located, the MAP needs to be calibrated in order to improve accuracy in estimating blood pressure.

The processor 130 may obtain an oscillogram based on the pulse wave signal measured from the object and by measuring force exerted between the object and the pulse wave signal, and may determine a first MAP based on the obtained oscillogram. For example, the processor 130 may determine, as the first MAP, a force value at a maximum amplitude point in the obtained oscillogram, but the first MAP is not limited thereto.

The processor 130 may extract additional information in an interval preceding a point of the first MAP in the oscillogram. The additional information may refer to information for calibrating the first MAP in order to improve accuracy in estimating blood pressure.

Figure 5:
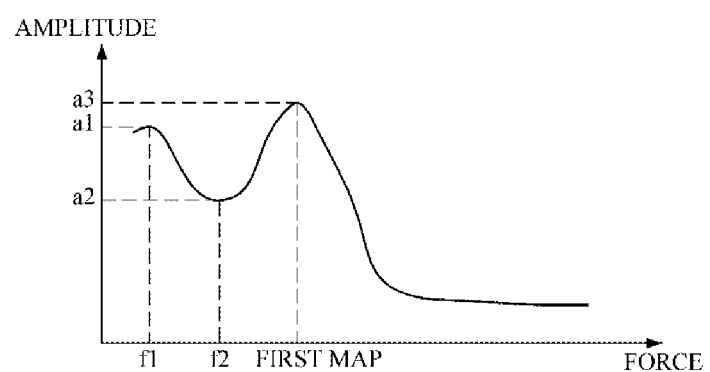
FIG. 5 is a diagram illustrating an example of an oscillogram of an object in which a plurality of blood vessels are located.

FIG. 5 is a diagram illustrating an example of an oscillogram of an object in which a plurality of blood vessels are located.

Referring to FIG. 5, the processor 130 may determine a peak point in the interval preceding the first MAP, and may extract, as additional information, an amplitude a1 and a force f1 at the determined peak point, an amplitude a2 and a force f2 at a valley point between the peak point and the first MAP point, and/or an amplitude a3 at the first MAP point. However, the additional information extracted by the processor 130 is not limited thereto.

If there is no peak point in the interval preceding the first MAP, the processor 130 may determine, as the peak point, a maximum amplitude point in an interval preceding the valley point which is located immediately before the first MAP (or a last valley point appearing before the first MAP).

Upon obtaining the additional information, the processor 130 may obtain a second MAP based on the first MAP and the additional information, and may estimate bio-information based on the obtained second MAP, thereby reducing an error in blood pressure estimation which is caused by the plurality of blood vessels.

For example, the processor 130 may obtain the second MAP by applying a ratio between at least two additional information items to the first MAP.

For example, the processor 130 may obtain the second MAP by applying a ratio between an amplitude at the first MAP point and an amplitude at the peak point to the first MAP, which may be represented by the following Equation 1.

$$\text{Second MAP} = \text{first MAP} \times (1 + a1/a3) \qquad [\text{Equation 1}]$$

Herein, a1 denotes the amplitude at the peak point, and a3 denotes the amplitude at the first MAP point. If the amplitude a1 at the peak point has a magnitude small enough to be ignored, the amplitude a1 is much smaller than the amplitude a3, such that the first MAP is approximated to the second MAP; and if not, it is highly likely that the first MAP is underestimated, such that the second MAP may be obtained by amplifying the first MAP by a ratio of a1/a3.

Further, the processor 130 may obtain the second MAP by applying a ratio between the amplitude at the valley point and the amplitude at the first MAP point to the first MAP, which may be represented by the following Equation 2.

$$\text{Second MAP} = \text{first MAP} \times (1 + a2/a3) \qquad \text{[Equation 2]}$$

Herein, a2 denotes the amplitude at the valley point, and a3 denotes the amplitude at the first MAP point. If the amplitude a2 at the valley point has a magnitude small enough to be ignored, the amplitude a2 is much smaller than the amplitude a3, such that the first MAP is approximated to the second MAP; and if not, it is highly likely that the first MAP is underestimated, such that the second MAP may be obtained by amplifying the first MAP by a ratio of a2/a3.

The processor 130 may estimate bio-information by using a bio-information estimation model based on the obtained second MAP. For example, the processor 130 may estimate blood pressure by applying the second MAP to a pre-defined blood pressure estimation model, and the blood pressure estimation model may be expressed in the form of various linear or non-linear combination functions, such as addition, subtraction, division, multiplication, logarithmic value, regression equation, and the like, with no particular limitation.

In another example, the processor 130 may obtain a second MAP which indicates a degree of underestimation based on a ratio between at least two additional information items, and a value obtained by subtracting a force value at the peak point from the first MAP.

For example, the processor 130 may obtain the second MAP by applying a ratio between the amplitude at the first MAP and the amplitude at the peak point to the value obtained by subtracting the force value at the peak point from the first MAP, which may be represented by the following Equation 3.

$$\text{Second MAP} = a1/a3 \times (\text{first MAP} - f1) \qquad \text{[Equation 3]}$$

Herein, a1 denotes the amplitude at the peak point, a3 denotes the amplitude at the first MAP point, and f1 denotes the force value at the peak point. In Equation 3, f1 corresponding to MAP of blood vessels other than the target blood vessel is excluded, such that the second MAP obtained using Equation 3 may indicate a degree of distortion of the first MAP.

Further, the processor 130 may obtain the second MAP by applying a ratio between the amplitude at the valley point and the amplitude at the first MAP point to a value obtained by subtracting the force value at the peak point from the first MAP, which may be represented by the following Equation 4.

$$\text{Second MAP} = a2/a3 \times (\text{first MAP} - f1) \qquad \text{[Equation 4]}$$

Herein, a2 denotes the amplitude at the valley point, a3 denotes the amplitude at the first MAP point, and f1 denotes the force value at the peak point. In Equation 4, f1 corresponding to MAP of blood vessels other than the target blood vessel is excluded, such that the second MAP obtained using Equation 4 may indicate a degree of distortion of the first MAP.

While the above methods of calibrating the first MAP are described with reference to Equations 1-4, these are merely examples and the embodiments are not limited thereto.

The processor 130 may estimate bio-information based on the first MAP and the second MAP by using a bio-information estimation model. For example, the processor 130 may estimate blood pressure by applying the first MAP and the second MAP to a pre-defined blood pressure estimation model, and the blood pressure estimation model may be expressed in the form of various linear or non-linear combination functions, such as addition, subtraction, division, multiplication, logarithmic value, regression equation, and the like, with no particular limitation.

Figure 6:
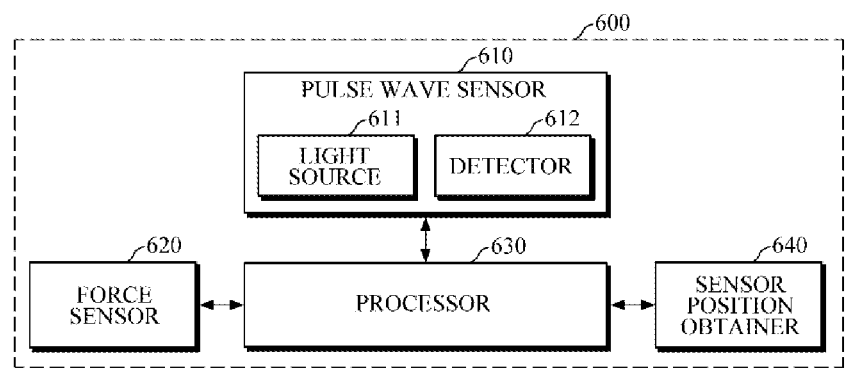
FIG. 6 is a block diagram illustrating an apparatus for estimating bio-information according to an example embodiment.

FIG. 6 is a block diagram illustrating an apparatus for estimating bio-information according to another example embodiment.

Referring to FIG. 6, an apparatus 600 for estimating bio-information according to an embodiment includes a pulse wave sensor 610, a force sensor 620, a processor 630, and a sensor position obtainer 640. The pulse wave sensor 610 includes a light source 611, and a detector 612. The pulse wave sensor 610, the force sensor 620, the processor 630, the light source 611, and the detector 612 may be the same or similar to those described in detail above with reference to FIG. 1.

When an object is in contact with the pulse wave sensor 610, the sensor position obtainer 640 may obtain sensor position information of the pulse wave sensor 610 located on the object. At least some of the functions of the sensor position obtainer 640 may be integrated into the processor 630.

The sensor position obtainer 640 may include a fingerprint sensor configured to obtain a fingerprint image of the object that is in contact with the pulse wave sensor 610. The fingerprint sensor may be disposed at an upper end or a lower end of the pulse wave sensor 610. The sensor position obtainer 640 may obtain sensor position information (e.g., information on a position of the pulse wave sensor on the object, which comes into contact with the pulse wave sensor) based on the fingerprint image obtained by the fingerprint sensor when the object is in contact with the pulse wave sensor 610. Further, the sensor position obtainer 640 may estimate a sensor position by analyzing a change in a fingerprint pattern based on the fingerprint image of the object. For example, when a finger applies pressure to the pulse wave sensor 610, a contact position between the finger and the pulse wave sensor 610 is pressed more than other positions of the finger, such that a distance between ridges or valleys of a fingerprint at the contact position between the finger and the pulse wave sensor 610 is relatively larger than other positions. If a distance between ridges or valleys of the fingerprint at a predetermined position of the finger is greater than or equal to a predetermined threshold value when compared to other positions, the sensor position obtainer 640 may obtain the position as a sensor position.

In addition, the sensor position obtainer 640 may obtain the sensor position information based on object images captured by an external image capturing device. The external image capturing device may be a camera module installed at a fixed location or a camera module mounted in a mobile device such as a smartphone and the like. For example, once the external image capturing device captures an image of the finger that is in contact with the pulse wave sensor 610, the sensor position obtainer 640 may receive the image of the finger through a communication module mounted in the apparatus 600 for estimating bio-information.

By analyzing a relative position between the pulse wave sensor 610 and the finger based on the image of the finger, the sensor position obtainer 640 may obtain the position of the finger, that is in contact with the pulse wave sensor 610, as a sensor position. Further, if the external image capturing device, having the function of obtaining a sensor position, obtains sensor position information by capturing an image of the finger, the sensor position obtainer 640 may receive the sensor position information from the external image capturing device through the communication module.

The processor 630 may guide a user on a contact position of the object based on the obtained sensor position information, or may obtain an oscillogram by selecting some of the plurality of pulse wave signals obtained by a plurality of channels.

For example, if the pulse wave sensor 610 has a single channel including one light source and one detector, the processor 630 may guide a user on a contact position of the object based on a blood vessel position of the object and sensor position information.

Figure 7A:
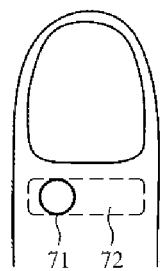
FIG. 7A illustrates an example of a pulse wave sensor having a single channel and FIG. 7B illustrates an example of a pulse wave sensor having multiple channels.

FIG. 7A is a diagram explaining an example of the pulse wave sensor 610 having a single channel 72. The processor 630 may display a finger image on a display, and may display a blood vessel position 71 of the finger which is superimposed on a position of the channel 72 of the pulse wave sensor 610, so as to guide a user to position the blood vessel of the finger on the channel 72.

In another example, if the pulse wave sensor 610 has a plurality of channels for measuring a plurality of pulse wave signals at multiple points of the object, the processor 630 may determine a proper channel based on the blood vessel position of the object and the sensor position.

Figure 7B:
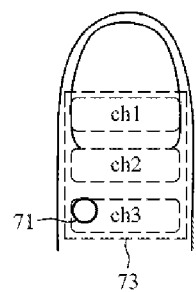

FIG. 7B is a diagram explaining an example of the pulse wave sensor 610 having multiple channels 73 for measuring a plurality of pulse wave signals at multiple points of the finger. Each of the channels ch1, ch2, and ch3 may include a light source and a detector. For example, upon receiving a request for estimating blood pressure, the processor 630 may select one of the multiple channels 73 by using the blood vessel position 71 of the finger and the sensor position information, and may drive the selected channel. For example, the processor 630 may drive a channel ch3, which is located closest to the blood vessel position 71, among the channels ch1, ch2, and ch3 of the pulse wave sensor 610. Alternatively, the processor 630 may obtain pulse wave signals from each of the channels ch1, ch2, and ch3 by simultaneously or sequentially driving the multiple channels 73 of the pulse wave sensor 610, and may select the channel ch3, which is located closest to the blood vessel position 71, as a channel for estimating blood pressure.

In addition, if the pulse wave sensor 610 has a plurality of channels, the processor 630 may select one of the plurality of channels based on a pulse wave signal corresponding to a predetermined position of the object or a pulse wave signal having a noise level less than or equal to a predetermined level, and may obtain an oscillogram based on the pulse wave signal obtained by the selected channel. For example, among a plurality of pulse wave signals measured by the plurality of channels, the processor 630 may determine a pulse wave signal corresponding to a specific position of a finger or may determine a pulse wave signal having a noise level less than or equal to a predetermined level by determining noise of the pulse wave signals, and may obtain an oscillogram by selecting at least one of the plurality of channels based on the pulse wave signal.

Figure 8:
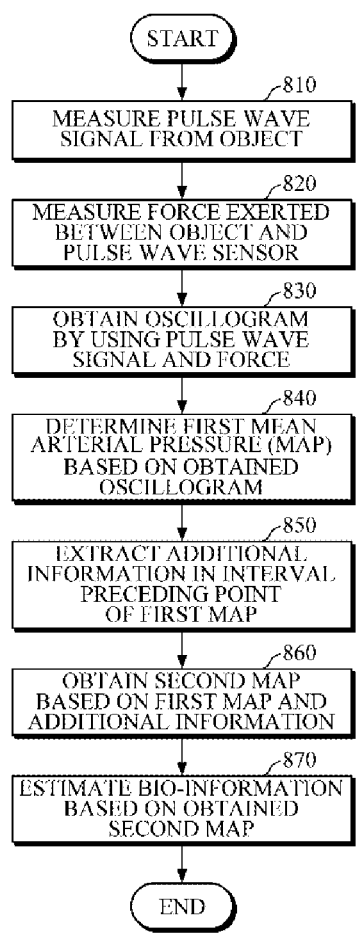
FIG. 8 is a flowchart illustrating a method of estimating bio-information according to an example embodiment.

FIG. 8 is a flowchart illustrating a method of estimating bio-information according to an example embodiment. The method of FIG. 8 is an example of a method of estimating bio-information performed by the aforementioned apparatuses 100 and 600 for estimating bio-information, which is described above in detail and thus will be briefly described below.

The apparatus for estimating bio-information may measure a pulse wave signal from an object through a pulse wave sensor in 810. For example, the pulse wave sensor may have a single channel to measure a pulse wave signal at a specific point of the object, or may have a plurality of channels to measure a plurality of pulse wave signals at multiple points of the object.

The apparatus for estimating bio-information may measure force exerted between the object and the pulse wave sensor through a force sensor in 820.

The apparatus for estimating bio-information may obtain an oscillogram by using the pulse wave signal and the force in 830. For example, if the pulse wave sensor having a plurality of channels acquires a plurality of pulse wave signals in 810, the apparatus for estimating bio-information may select one of the plurality of channels based on a pulse wave signal corresponding to a predetermined position of the object or a pulse wave signal having a noise level less than or equal to a predetermined level, and may obtain an oscillogram based on the pulse wave signal obtained by the selected channel.

The apparatus for estimating bio-information may determine a first mean arterial pressure (MAP) based on the obtained oscillogram in 840. For example, the apparatus for estimating bio-information may determine a force value at a maximum amplitude point in the obtained oscillogram to be the first MAP.

The apparatus for estimating bio-information may extract additional information in an interval preceding a point of the first MAP of the oscillogram in 850. For example, the apparatus for estimating bio-information may determine a peak point in the interval preceding the first MAP, and may extract, as the additional information, at least one of an amplitude and a force at the determined peak point, an amplitude and a force at a valley point between the peak point and the first MAP point, and an amplitude at the first MAP point. If there is no peak point in the interval preceding the first MAP, the apparatus for estimating bio-information may determine a maximum amplitude point in an interval preceding the valley point which is located immediately before the first MAP.

The apparatus for estimating bio-information may obtain a second MAP based on the first MAP and the additional information in 860. For example, the apparatus for estimating bio-information may obtain the second MAP by applying a ratio between at least two additional information items to the first MAP. For example, the apparatus for estimating bio-information may obtain the second MAP by applying a ratio between an amplitude at the first MAP point and an amplitude at the peak point to the first MAP, or by applying a ratio between an amplitude at the first MAP point and an amplitude at the valley point to the first MAP. In another example, the apparatus for estimating bio-information may obtain the second MAP based on a ratio between at least two additional information items, and a value obtained by subtracting a force value at the peak point from the first MAP. For example, the apparatus for estimating bio-information may obtain the second MAP by applying a ratio between the amplitude at the first MAP and the amplitude at the peak point to a value obtained by subtracting the force value at the peak point from the first MAP, or may obtain the second MAP by applying a ratio between the amplitude at the first MAP and the amplitude at the valley point to a value obtained by subtracting the force value at the peak point from the first MAP. However, the above examples are described for illustrative purposes only and the embodiments are not limited thereto.

The apparatus for estimating bio-information may estimate bio-information based on the obtained second MAP in 870. For example, the apparatus for estimating bio-information may estimate bio-information based on the first MAP and/or the second MAP by using a bio-information estimation model.

Figure 9:
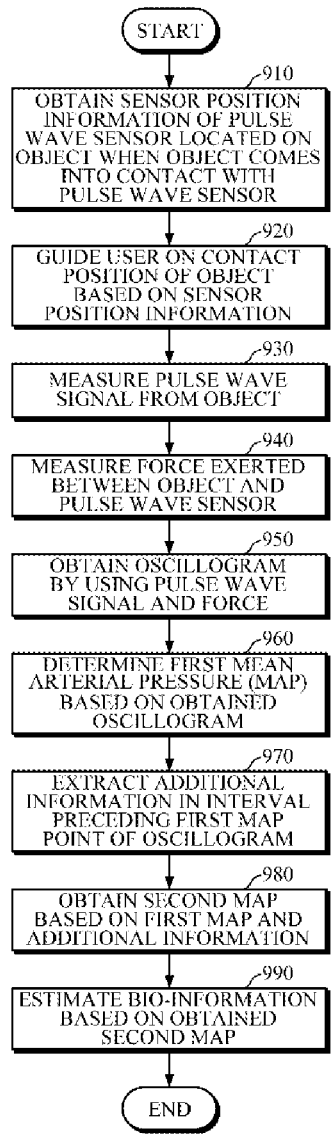
FIG. 9 is a flowchart illustrating a method of estimating bio-information according to an example embodiment.

FIG. 9 is a flowchart illustrating a method of estimating bio-information according to another example embodiment. The method of FIG. 9 is an example of a method of estimating bio-information that may be performed by the aforementioned apparatuses 100 and 600 for estimating bio-information, which is described above in detail and thus will be briefly described below.

When an object comes into contact with the pulse wave sensor, the apparatus for estimating bio-information may obtain sensor position information of the pulse wave sensor located on the object when the object comes into contact with the pulse wave sensor in 910. For example, the apparatus for estimating bio-information may obtain the sensor position information based on a fingerprint image obtained by the fingerprint sensor when the object is in contact with the pulse wave sensor, or may obtain the sensor position information based on an image of the object obtained by an external image capturing means (or image capturing device such as, e.g., a camera).

The apparatus for estimating bio-information may guide a user on a contact position of the object based on the sensor position information in 920. For example, if the pulse wave sensor has a single channel, the apparatus for estimating bio-information may guide the user on the contact position of the object based on a blood vessel position of the object and the sensor position information.

The apparatus for estimating bio-information may measure a pulse wave signal from the object at the contact position in 930, may measure force exerted between the object and the pulse wave sensor in 940, and may obtain an oscillogram by using the measured pulse wave signal and the force in 950.

The apparatus for estimating bio-information may determine a first mean arterial pressure (MAP) based on the obtained oscillogram in 960.

The apparatus for estimating bio-information may extract additional information in an interval preceding the first MAP point of the oscillogram in 970.

The apparatus for estimating bio-information may obtain a second MAP based on the first MAP and the additional information in 980. For example, the apparatus for estimating bio-information may obtain the second MAP by applying a ratio between at least two additional information items to the first MAP. Alternatively, the apparatus for estimating bio-information may obtain the second MAP, which indicates a degree of underestimation, based on the ratio between at least two additional information items, and a value obtained by subtracting the force value at the peak point from the first MAP.

The apparatus for estimating bio-information may estimate bio-information based on the obtained second MAP in 990. For example, the apparatus for estimating bio-information may estimate bio-information based on the first MAP and/or the second MAP by using a bio-information estimation model.

Figure 10:
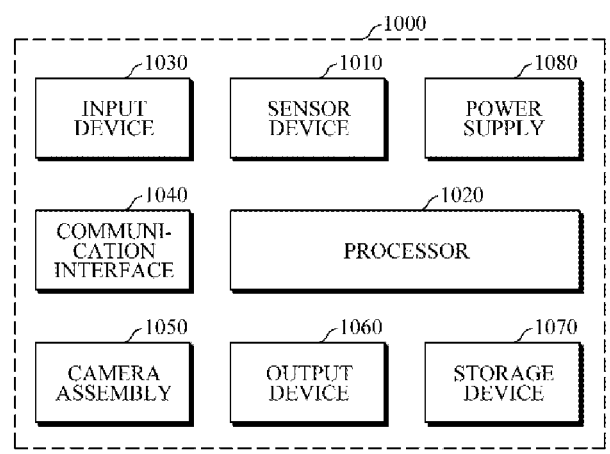
FIG. 10 is a block diagram illustrating an electronic device including an apparatus for estimating bio-information according to an example embodiment.

FIG. 10 is a block diagram illustrating an example of an electronic device including an apparatus for estimating bio-information according to an example embodiment.

In an example embodiment, an electronic device 1000 may include, for example, a wearable device of various types, e.g., a smart watch, a smart band, smart glasses, smart earphones, a smart ring, a smart patch, and a smart necklace, and a mobile device such as a smartphone, a tablet PC, etc., or home appliances or various Internet of Things (IoT) devices (e.g., home IoT device) based on Internet of Things (IoT) technology.

Referring to FIG. 10, the electronic device 1000 may include a sensor device 1010, a processor 1020, an input device 1030, a communication interface 1040, a camera assembly 1050, an output device 1060, a storage device 1070, and a power supply 1080. All the components of the electronic device 1000 may be integrally mounted in a specific device or may be distributed in two or more devices.

The sensor device 1010 may include the pulse wave sensor 110 and/or 610 and the force sensor 120 and/or 620 of the aforementioned apparatuses 100 and 600 for estimating bio-information. The pulse wave sensor 110 and/or 610 may include one or more light sources 111 and 611 and one or more detectors 112 and/or 612, and when an object comes into contact with the pulse wave sensor 110 and/or 610, the pulse wave sensor 110 and/or 610 may acquire a pulse wave signal from the object. The force sensor 120 and/or 620 may be disposed at an upper end or a lower end of the pulse wave sensor 110 and/or 610, and may measure a contact force exerted between the object and the pulse wave sensor 110 and/or 610.

The sensor device 1010 may include sensors for performing various other functions, for example, a gyro sensor, a Global Positioning System (GPS), and the like.

The processor 1020 may execute programs, stored in the storage device 1070, to control components connected to the processor 1020, and may perform various data processing or computation. The processor 1020 may include a main processor, e.g., a central processing unit (CPU) or an application processor (AP), etc., and an auxiliary processor, e.g., a graphics processing unit (GPU), an image signal processor (ISP), a sensor hub processor, or a communication processor (CP), etc., which is operable independently from, or in conjunction with, the main processor.

The processor 1020 may include the processors of the aforementioned apparatuses 100 and 600 for estimating bio-information. For example, in response to a user's request for estimating bio-information, the processor 1020 may transmit a control signal to the sensor device 1010, and may estimate bio-information by using the pulse wave signal and the force signal received from the sensor device 1010. The processor 1020 may estimate bio-information by using an oscillogram of the object, and may transmit the estimated bio-information to an external device by using the communication interface 1040.

For example, the processor 1020 may obtain azo oscillogram by using the pulse wave signal and the force signal, may determine a first mean arterial pressure (MAP) based on the obtained oscillogram, may extract additional information in an interval preceding a point of the first MAP of the oscillogram, may obtain a second MAP based on the first MAP and the additional information, and may estimate bio-information based on the obtained second MAP.

Further, the processor 1020 may determine a peak point in the interval preceding the first MAP, and may extract, as the additional information, at least one of an amplitude and a force at the determined peak point, an amplitude and a force at a valley point between the peak point and the first MAP point, and an amplitude at the first MAP point, and may obtain the second MAP based on the first MAP and a ratio between at least two additional information items.

The input device 1030 may receive a command and/or data to be used by each component of the electronic device 1000, from a user and the like. The input device 1030 may include, for example, a microphone, a mouse, a keyboard, or a digital pen (e.g., a stylus pen).

The communication interface 1040 may support establishment of a direct (e.g wired) communication channel and/or a wireless communication channel between the electronic device 1000 and other electronic device, a server, or the sensor device 1010 within a network environment, and support communication via the established communication channel. The communication interface 1040 may include one or more communication processors that are operable independently from the processor 1020 and supports a direct communication and/or a wireless communication.

The communication interface 1040 may include a wireless communication module, e.g., a cellular communication module, a short-range wireless communication module, or a global navigation satellite system (GNSS) communication module, etc., and/or a wired communication module, e.g., a local area network (LAN) communication module, a power line communication (PLC) module, and the like. These various types of communication modules may be integrated into a single chip, or may be separately implemented as multiple chips. The wireless communication module may identify and authenticate the electronic device 1000 in a communication network by using subscriber information (e.g., international mobile subscriber identity (IMSI)) stored in a subscriber identification module.

The camera assembly 1050 may capture still images or moving images. The camera assembly 1050 may include a lens assembly having one or more lenses, image sensors, image signal processors, and/or flashes. The lens assembly included in the camera assembly 1050 may collect light emanating from a subject to be imaged.

The output device 1060 may visually and/or non-visually output data generated or processed by the electronic device 1000. The output device 1060 may include a sound output device, a display device, an audio module, and/or a haptic module.

The sound output device may output sound signals to the outside of the electronic device 1000. The sound output device may include a speaker and/or a receiver. The speaker may be used for general purposes, such as playing multimedia or playing record, and the receiver pray be used for incoming calls. The receiver may be implemented separately from, or as part of, the speaker.

The display device may visually provide information to the outside of the electronic device 1000. The display device may include, for example, a display, a hologram device, or a projector and control circuitry to control the devices. The display device may include touch circuitry adapted to detect a touch, and/or sensor circuitry (e.g., pressure sensor) adapted to measure the intensity of force incurred by the touch.

The audio module may convert sound into an electrical signal or vice versa. The audio module may obtain the sound via the input device, or may output the sound via the sound output device, and/or a speaker and/or a headphone of another electronic device directly or wirelessly connected to the electronic device 1000.

The haptic module may convert an electrical signal into a mechanical stimulus (e.g., vibration, motion) or electrical stimulus which may be recognized by a user by tactile sensation or kinesthetic sensation. The haptic module may include, for example, a motor, a piezoelectric element, and/or an electric stimulator.

The storage device 1070 may store driving conditions for driving the sensor device 1010, and various data used for other components of the electronic device 1000. The various data may include, for example, software and input data and/or output data for a command related thereto. The storage device 1070 may include a volatile memory and/or a non-volatile memory.

The power supply 1080 may manage power supplied to the electronic device 1000. The power supply 1080 may be implemented as part of a power management integrated circuit (PMIC). The power supply 1080 may include a battery, including a primary cell which is not rechargeable, a secondary cell which is rechargeable, and/or a fuel cell.

Figure 11:
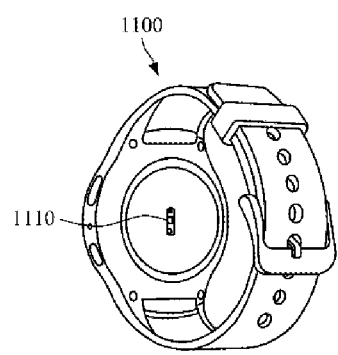
FIG. 11 is a diagram illustrating a wristwatch wearable device including an apparatus for estimating bio-information according to an example embodiment.
Figure 12:
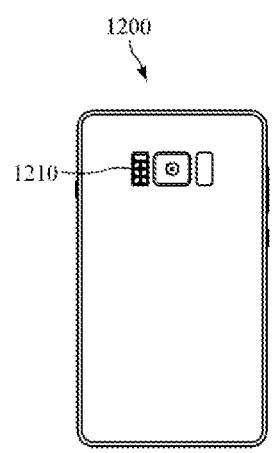
FIG. 12 is a diagram illustrating a mobile device including an apparatus for estimating bio-information according to an example embodiment.

FIGS. 11 and 12 are diagrams illustrating examples of structures of an apparatus for estimating bio-information according to an example embodiments.

Referring to FIG. 11, a wristwatch wearable device 1100 may include an apparatus for estimating bio-information according to an example embodiment (e.g., the electronic device 1000 shown in FIG. 10), and may include a main body and a wrist strap. A display is provided on a front surface of the main body, and may display various application screens, including time information, received message information, and the like. A sensor device 1110 may be disposed on a rear surface of the main body to measure a pulse wave signal and a force signal for estimating bio-information. However, the location of the sensor device 1110 is not limited thereto.

Referring to FIG. 12, a mobile device 1200 such as a smartphone may include an apparatus for estimating bio-information according to an example embodiment (e.g., the electronic device 1000 shown in FIG. 10).

The mobile device 1200 may include a housing and a display panel. The housing may form an exterior of the mobile device 1200. The housing has a first surface, on which a display panel and a cover glass may be disposed sequentially, and the display panel may be exposed to the outside through the cover glass. A sensor device 1210, a camera module (or camera assembly) and/or an infrared sensor, and the like may be disposed on a second surface of the housing. However, the location of sensor device 1210 is not limited thereto. When a user transmits a request for estimating bio-information by executing an application and the like installed in the mobile device 1200, the mobile device 1200 may estimate bio-information by using the sensor device 1210, and may provide the estimated bio-information value as images and/or sounds to a user.

Figure 13:
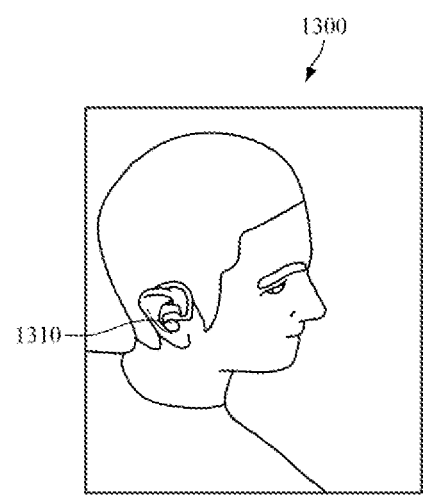
FIG. 13 is a diagram illustrating an ear-wearable device including an apparatus for estimating bio-information according to an example embodiment.

Referring to FIG. 13, an ear-wearable device 1300 may include an apparatus for estimating formation according to an example embodiment (e.g., the electronic device 1000 shown in FIG. 10).

The ear-wearable device 1300 may include a main body and an ear strap. A user may wear the ear-wearable device 1300 by hanging the ear strap on a user's auricle. The ear strap may be omitted depending on the type of ear-wearable device 1300. The main body may be inserted into the external auditory meatus. A sensor device 1310 may be mounted in the main body. However, the location of the sensor device 1310 is not limited thereto. The ear-wearable device 1300 may provide a component estimation result as sounds to a user, or may transmit the estimation result to an external device, e.g., a mobile device, a tablet PC, a personal computer, etc., through a communication module provided in the main body.

The disclosure may be provided as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium may be distributed over a plurality of computer systems connected to a network so that a computer-readable code is written thereto and executed therefrom in a decentralized manner. Functional programs, codes, and code segments for implementing the disclosure may be readily deduced by programmers of ordinary skill in the art to which the disclosure pertains.

At least one of the components, elements, modules or units represented by a block in the drawings may be embodied as various numbers of hardware, software and/or firmware structures that execute respective functions described above, according to an example embodiment. According to example embodiments, at least one of these components may use a direct circuit structure, such as a memory, a processor, a logic circuit, a look-up table, etc. that may execute the respective functions through controls of one or more microprocessors or other control apparatuses. Also, at least one of these components may be specifically embodied by a module, a program, or a part of code, which contains one or more executable instructions for performing specified logic functions, and executed by one or more microprocessors or other control apparatuses. Further, at least one of these components may include or may be implemented by a processor such as a central processing unit (CPU) that performs the respective functions, a microprocessor, or the like. Two or more of these components may be combined into one single component which performs all operations or functions of the combined two or more components. Also, at least part of functions of at least one of these components may be performed by another of these components. Functional aspects of the above example embodiments may be implemented in algorithms that execute on one or more processors. Furthermore, the components represented by a block or processing steps may employ any number of related art techniques for electronics configuration, signal processing and/or control, data processing and the like.

While the disclosure has been described with reference to example embodiments thereof, it will be apparent to those of ordinary skill in the art that various changes and modifications may be made thereto without departing from the spirit and scope of the disclosure as set forth in the following claims.

What is claimed is:

1. An apparatus for non-invasively estimating bio-information, the apparatus comprising:
a pulse wave sensor configured to measure a pulse wave signal from an object;
a force sensor configured to measure a force exerted between the object and the pulse wave sensor;
a processor configured to:
obtain an oscillogram by using the pulse wave signal and the force,
determine a first mean arterial pressure (MAP) based on the obtained oscillogram,
extract additional information in an interval preceding a point of the first MAP of the oscillogram,
obtain a second MAP based on the first MAP and the additional information, and
estimate the bio-information based on the obtained second MAP; and
a display configured to output the estimated bio-information,
wherein the processor is further configured to:
determine, as the first MAP, a force value at a maximum amplitude point in the obtained oscillogram,
determine a peak point in the interval preceding the first MAP, and
extract, as the additional information, at least one of an amplitude and a force at the determined peak point, an amplitude and a force at a valley point between the peak point and the point of the first MAP, and an amplitude at the point of the first MAP,
wherein the processor is further configured to:
extract at least two of the additional information, and
obtain the second MAP by applying a ratio between values of the at least two of the additional information to the first MAP,
wherein the pulse wave sensor comprises:
at least one light source configured to emit light onto the object; and
at least one detector configured to detect light scattered or reflected from the object, and
wherein the processor is further configured to display a finger image on the display, and to display a blood vessel position of a finger which is superimposed on a position of a channel of the pulse wave sensor to guide a user to position a blood vessel of the finger on the channel.

2. The apparatus of claim 1, wherein the processor is further configured to, based on a determination that the peak point does not exist in the interval preceding the first MAP, determine, as the peak point, a maximum amplitude point in an interval preceding the valley point, the valley point being a last valley point before the first MAP.

3. The apparatus of claim 1, wherein the at least two of the additional information comprise the amplitude at the point of the first MAP and the amplitude at the peak point to the first MAP, and
wherein the processor is further configured to obtain the second MAP by applying a ratio between the amplitude at the point of the first MAP and the amplitude at the peak point to the first MAP.

4. The apparatus of claim 1, wherein the at least two of the additional information comprise the amplitude at the point of the first MAP and the amplitude at the valley point to the first MAP, and
wherein the processor is further configured to obtain the second MAP by applying a ratio between the amplitude at the point of the first MAP and the amplitude at the valley point to the first MAP.

5. The apparatus of claim 1, wherein the processor is further configured to estimate the bio-information based on the second MAP by using a bio-information estimation model.

6. The apparatus of claim 1, wherein the processor is further configured to:
extract at least three of the additional information including the force at the peak point, and
obtain the second MAP based on a ratio between values of at least two of the additional information of the at least three of the additional information, and further based on a first value obtained by subtracting a value of the force at the peak point from the first MAP.

7. The apparatus of claim 6, wherein the processor is further configured to obtain the second MAP by applying a ratio, between the amplitude at the point of the first MAP and the amplitude at the peak point, to the first value.

8. The apparatus of claim 6, wherein the processor is further configured to obtain the second MAP by applying a ratio, between the amplitude at the point of the first MAP and the amplitude at the valley point, to the first value.

9. The apparatus of claim 6, wherein the processor is further configured to estimate the bio-information based on the first MAP and the second MAP by using a bio-information estimation model.

10. The apparatus of claim 1, further comprising a sensor position obtainer configured to obtain sensor position information of the pulse wave sensor, the sensor position information indicating a position of the pulse wave sensor on the object, which comes into contact with the pulse wave sensor,
wherein the processor is further configured to control to guide the user on a contact position of the object based on the sensor position information.

11. The apparatus of claim 10, wherein the sensor position obtainer comprises a fingerprint sensor configured to obtain a fingerprint image of the object that comes into contact with the pulse wave sensor, and
wherein the sensor position obtainer is further configured to obtain the sensor position information based on the fingerprint image obtained by the fingerprint sensor.

12. The apparatus of claim 10, wherein the sensor position obtainer is further configured to obtain the sensor position information based on an image of the object that comes into contact with the pulse wave sensor, the image being acquired by an external image capturing device.

13. The apparatus of claim 1, wherein the pulse wave sensor has a plurality of channels for measuring pulse wave signals at a plurality of points of the object, and
wherein the processor is further configured to:
select at least one channel of the plurality of channels based on a pulse wave signal corresponding to a predetermined position of the object that comes into contact with the pulse wave sensor or based on a pulse wave signal having a noise level less than or equal to a predetermined level, and
obtain the oscillogram based on the pulse wave signal obtained by the selected at least one channel.

14. The apparatus of claim 1, wherein the bio-information comprises blood pressure.

15. A method of non-invasively estimating bio-information, the method comprising:
displaying a finger image on a display and displaying a blood vessel position of a finger which is superimposed on a position of a channel of a pulse wave sensor which has at least one light source and at least one detector to guide a user to position a blood vessel of the finger on the channel;
measuring, by using the pulse wave sensor, a pulse wave signal from an object;
measuring a force exerted between the object and the pulse wave sensor;
obtaining an oscillogram by using the pulse wave signal and the force;
determining a first mean arterial pressure (MAP) based on the obtained oscillogram;
extracting additional information in an interval preceding a point of the first MAP of the oscillogram;
obtaining a second MAP based on the first MAP and the additional information; and
estimating the bio-information based on the obtained second MAP,
wherein the determining of the first MAP comprises determining a force value at a maximum amplitude point in the obtained oscillogram to be the first MAP,
wherein the extracting the additional information comprises determining a peak point in the interval preceding the first MAP, and extracting, as the additional information, at least one of an amplitude and a force at the determined peak point, an amplitude and a force at a valley point between the peak point and the point of the first MAP, and an amplitude at the point of the first MAP,
wherein the extracting comprises extracting at least two of the additional information, and
wherein the obtaining the second MAP comprises obtaining the second MAP by applying a ratio between values of the at least two of the additional information to the first MAP.

16. The method of claim 15, wherein the extracting the additional information comprises, based on a determination that the peak point does not exist in the interval preceding the first MAP, determining, as the peak point, a maximum amplitude point in an interval preceding the valley point, the valley point being a last valley point before the first MAP.

17. The method of claim 15, wherein the estimating the bio-information comprises estimating the bio-information based on the second MAP by using a bio-information estimation model.

18. The method of claim 15, wherein the extracting comprises extracting at least three of the additional information including the force at the peak point, and
wherein the obtaining the second MAP comprises obtaining the second MAP based on a ratio between values of the at least two of the additional information of the at least three of the additional information, and further based on a value obtained by subtracting a value of the force at the peak point from the first MAP.

19. The method of claim 18, wherein the estimating the bio-information comprises estimating the bio-information based on the first MAP and the second MAP by using a bio-information estimation model.

20. The method of claim 15, further comprising:
obtaining sensor position information of the pulse wave sensor, the sensor position information indicating a position of the pulse wave sensor on the object, which comes into contact with the pulse wave sensor; and
controlling to guide the user on a contact position of the object based on the sensor position information.

* * * * *